United States Patent [19]

Lee et al.

[11] Patent Number: 4,537,661

[45] Date of Patent: Aug. 27, 1985

[54] TECHNIQUE FOR MONITORING THE OXIDATION/REDUCTION POTENTIAL CHARACTERISTICS OF A STEAM ENVIRONMENT

[75] Inventors: Pang K. Lee, Murrysville; William M. Hickam, Churchill Borough, both of Pa.

[73] Assignee: Westinghouse Electric Corp., Pittsburgh, Pa.

[21] Appl. No.: 613,832

[22] Filed: May 24, 1984

[51] Int. Cl.³ .............................. G01N 27/46
[52] U.S. Cl. .................... 204/1 T; 204/426; 204/427; 204/428; 415/118
[58] Field of Search ............... 204/1 S, 421–429

[56] References Cited

U.S. PATENT DOCUMENTS 4,098,650  7/1978  Sayles ............................ 204/427
4,209,378  6/1980  Schinohara et al. ............ 204/424

Primary Examiner—T. Tung
Attorney, Agent, or Firm—Thomas R. Trempus

[57] ABSTRACT

The invention provides a method for the continuous monitoring of the oxygen or hydrogen concentrations in a steam system with a solid electrolyte oxygen analyzer. The operating temperature of the analyzer is adjusted to about 500° C. and the reference gas used for the analyzer is air or oxygen-inert gas mixture. Under operating conditions, an oxygen or hydrogen level of low parts per billion in superheated or saturated steam can be identified and measured. This technique is specifically useful for continuously monitoring the air inleakage, that is, the oxygen contents in steam and for controlling the corrosion intensity that is, the hydrogen levels in steam in, for example, steam turbine systems in power plants.

5 Claims, 7 Drawing Figures

TECHNIQUE FOR MONITORING THE OXIDATION/REDUCTION POTENTIAL CHARACTERISTICS OF A STEAM ENVIRONMENT

FIELD OF THE INVENTION

The invention relates to a technique for monitoring a steam environment. More particularly, the invention provides a method and an apparatus for the continuous monitoring of the oxidation and/or reduction potential characteristics in a steam environment. The invention also provides for the continuous monitoring of air leakage and for the controlling of corrosion intensity in steam systems.

BACKGROUND OF THE INVENTION

Oxygen inleakage is one of the significant causes of corrosion in power plants, in general, and turbines and steam generators in particular. The concentration of oxygen in the secondary steam/condensate cycle can be changed by both non-corroding and corroding chemical reactions. Hydrazine is added to condensate and it scavenges oxygen by chemical reaction to form water. "Corrosion" hydrogen can also react with oxygen to form water. Organics present in the cycles can scavenge oxygen by chemical reactions thus leading to the formation of carbon dioxide, carbon monoxide and water. Ammonia also reacts with oxygen at high temperatures.

The presence of such volatile oxygen scavengers or reducing agents can alter the metal/metal oxide composition present in the steam/condensate systems and on the surface of materials exposed to the steam cycle. Whether metallic impurities exist in the steam as oxides or as metals is influenced by the oxidation/reduction potential characteristics of the steam. Reducing atmospheres favor the existence of the metallic form and oxidizing atmospheres favor the existence of the metallic oxide forms. Since copper/copper oxides can react with iron/iron oxides and alter their chemical form, the control of the chemical state of copper impurities in the steam is expected to exert a strong influence on the level of iron transport.

To fully optimize the chemistry of both the liquid and gaseous parts of the secondary cycle, for maximum iron/iron oxide stability against chemical reactions and minimum iron transport, it is necessary that chemicals be added to both the condensate and the steam. The introduction of chemical additives to the steam and condensate make it possible to independently modify the chemistry of both the liquid phase and the steam phase. Since corrosion mechanisms operative in the liquid and gaseous phases differ, this dual approach to corrosion control has some level of merit. This approach permits the chemical compensation for impurities formed in the steam generator and not present in the liquid phase, for example, organic acids.

Presently, no methods are employed to monitor and control the oxidation/reduction potential characteristic of steam in today's operating power plants. In such power plants, air inleakage in the steam condenser has been one of the major problems causing power plant failures. The corrosion failure from disc cracking in low pressure steam turbines is also related to air inleakage in the turbine system where the steam pressure becomes lower than the atmosphere pressure. Metal oxidation by free oxygen at high temperatures is a severe problem. However, the intensity of the corrosion process taking place in any steam-water system can also be traced to the variation of hydrogen concentrations in the steam. The appearance of hydrogen in the steam can be due to a number of causes. For example, the corrosion of the metal components under the action of the water or steam, a catalytic decomposition of hydrazine when the boiler feedwater is treated with this reagent, thermal decomposition of organic impurities, and thermal disassociation of the water itself. Of these examples, the main cause is the interaction of water or steam with the steel components. The formation of dense and adherent magnetite film protects the steel from further interaction. Several factors can influence the integrity of the protective film. The disturbance of flow rate, an excess thermal stress associated with the sharp change in local temperature, and the presence of oxidizing deposits in the magnetite film are such factors. Once the protected surface film ruptures, the steam comes into contact with the steel and more hydrogen will appear. It has been a long standing goal to develop a technique to continuously monitor the oxygen and hydrogen concentrations in operating steam systems in order to detect air inleakage and to control corrosion intensities.

It is, therefore, an object of this invention to provide a method for monitoring the oxidation/reduction potential characteristics of a steam environment.

It is a further object of this invention to provide a method for operating the solid electrolyte electrochemical cell so as to make possible the detection of low concentration levels of oxygen and hydrogen in a steam environment.

SUMMARY OF THE INVENTION

The invention provides a method for monitoring the oxidation and/or reduction potential characteristics of a steam environment. The method includes the steps of: (1) sampling a constituent of interest in the steam environment (2) determining the partial pressure of the sampled constituent of interest, and (3) comparing the monitored and/or determined partial pressure of the sample with a set of predetermined criteria. The sampling can be effected with either in-situ gas analyzer or an externally mounted gas analyzer contacted with an extracted sample. The predetermined criteria reflect known oxidation reduction potential characteristics. The invention also provides a method for operating a solid electrolyte electrochemical cell assembly of the type which generates an electrical output signal. The solid electrolyte electrochemical cell assembly has a solid electrolyte member having a first electrode disposed in contact with a first surface thereof and a second electrode disposed in contact with the opposite surface. The solid electrolyte is disposed in the cell assembly such that the first surface of the solid electrolyte member is exposed to a reference gas and the opposite surface of the solid electrolyte member is exposed to an environment of interest. The solid electrolyte member generates an electrical signal reflective of the gas partial pressure in contact therewith. The cell assembly includes heating means operatively associated therewith for effecting the controllable heating of the solid electrolyte member. The new operational technique for use with such a sensor assembly includes the steps of: (1) disposing the cell assembly in the steam environment so that the second surface of the solid electrolyte member is in communication with the steam environment, (2) providing a reference gas of determinable content in communication with the first surface of the solid electrolyte member, (3) heating the solid electrolyte member to a temperature at which low concentration levels of oxygen and hydrogen are distinguishable from one another, and (4) measuring the electrical signal generated by the solid electrolyte member as a function of the oxygen or hydrogen content in the steam environment. The measured electrical signal generated by the sensor assembly provides an indication of the oxidation or reduction potential present in the monitored steam.

BRIEF DESCRIPTION OF THE DRAWINGS

The above as well as other features and advantages of this invention will become apparent through consideration of the detailed description in connection with the accompanying drawings in which.

DETAILED DESCRIPTION OF THE INVENTION

The invention provides a technique for monitoring the oxidation/reduction potential characteristics of a steam environment through the use of a solid electrolyte electrochemical cell. The invention also provides a unique method for operating a solid electrolyte electrochemical cell assembly which has heretofore been used primarily in industrial applications for combustion product gas measuring. More particularly, the apparatus for use with this invention is an oxygen analyzing device of the type which may be inserted directly into a gas stream of an environment of interest such as a flue, stack or boiler. This gas analyzer device provides instantaneous, in-situ, measurement of oxygen. Such a gas analyzer device which has been found to be quite useful in effecting the technique of this invention is disclosed in U.S. Pat. No. 3,928,161 entitled "Gas Measuring Probe for Industrial Applications" and is assigned to the assignee of the present application. U.S. Pat. No. 3,928,161 is incorporated by reference as if fully set forth herein.

Figure 1:
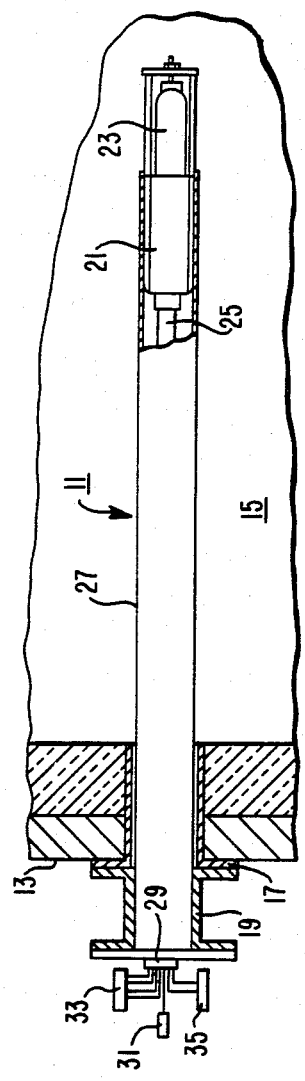
FIG. 1 is a schematic illustration of a solid electrolyte electrochemical cell sensor assembly which can be utilized for the continuous monitoring of a steam environment according to the teachings of this invention.

Turning now to FIG. 1, there is illustrated a typical embodiment of a solid electrolyte sensor assembly 11 inserted within the wall 13 which encloses an environment of interest generally indicated at 15 in order to monitor a constituent of interest within that environment. Typically, the wall 13 is provided with a flange 17 by which the probe or sensor assembly 11 is secured by means of its own flange 19. The probe assembly 11 is comprised of a solid electrolyte oxygen sensor assembly 21, a porous protective shield 23 and tubular extension member 25 for positioning the combination of the sensor assembly 21 and protective shield 23 within the stationary tubular support member 27. Supporting apparatus for the operation of the solid electrolyte cell assembly 21 is typically illustrated in U.S. Pat. No. 3,546,086, entitled "Device for Oxygen Measurement" issued Dec. 8, 1970 and assigned to the assignee of the present invention. The supporting apparatus includes an interconnect assembly 29 for supplying a desired reference gas from a reference source 31 to the cell assembly 21 and for providing signal leads for a temperature sensing element in the cell assembly 21 for monitoring cell temperature by the temperature controller 33. The electrical signal developed by the solid electrolyte electrochemical cell assembly 21 in response to the content of a constituent of interest within the monitored environment is transmitted to the measuring or recording apparatus 35 through the interconnect assembly 29.

Figure 2:
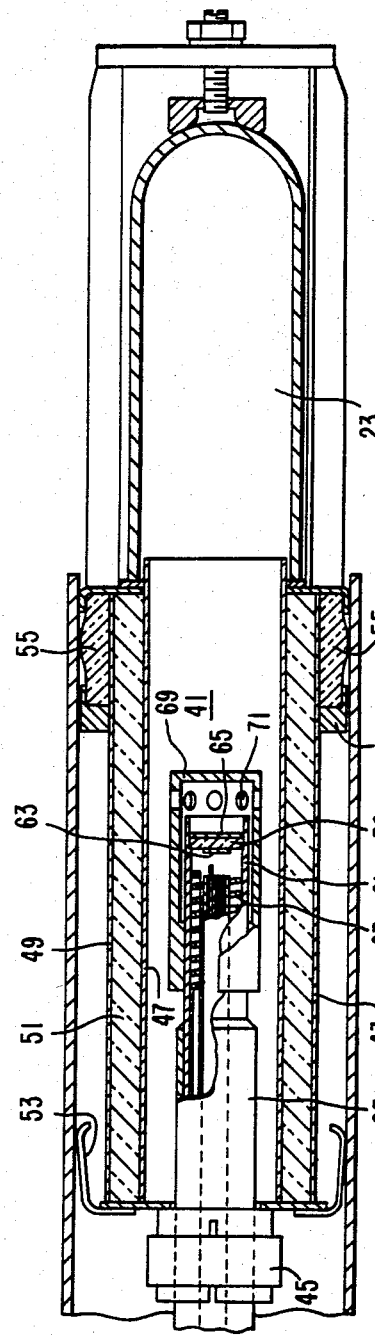
FIG. 2 is a detailed sectional schematic illustration of the oxygen probe assembly of FIG. 1.

There is illustrated in FIG. 2 a sectional schematic representation of a solid electrolyte sensor assembly 21. The assembly 21 is comprised of solid electrolyte cell assembly 41 which is secured to the tubular extension member 25 and which in turn is fixedly secured within a tubular insulating member 43 by the clamp 45. The tubular thermal insulating member 43 is in the form of a tubular can typically constructed of inner and outer walls 47 and 49 within which is packed a thermal insulating material 51. The insulating material functions to effectively insulate the temperature sensitive solid electrolyte cell assembly 41 from heat transfer from the temperature environment existing within the environment of interest. Attached to the tubular member 43 are spring members 53 which in conjunction with the cylindrical sealing collar 55 function to stably align and position the combination of the sensor assembly 21 and the protective shield assembly 23 within the stationary tubular member 27. The sealing collar 55 which is in the form of a collar positioned about the tubular thermal insulating member 43 is illustrated as comprised of the same thermal insulating material utilized within the wall of the tubular thermal insulating member 43 and provides an effective diameter sufficient to provide essentially a force fit of the combination of assemblies 21 and 23 within the tubular member 27. The sealing collar 55 in addition to providing alignment of the assembly combination also serves to provide a barrier whereby particles in the environment of interest are prevented from traveling within the tubular member 27, thus avoiding a build-up of foreign matter which could adversely affect the insertion and removal of the probe assembly 11. The thermal insulating material utilized with the tubular thermal protection device 43 and used as the sealing collar 55 can be one of many thermal insulating materials available. The effective diameter of the sealing collar 55 can be varied by the positioning of the adjustable clamp 57.

The solid electrolyte cell assembly 41 is comprised of a solid electrolyte member 59 illustrated in the form of a disc sealed to form the closed end of the tubular support member 61 which has the opposite ends secured to the tubular extension member 25. Disposed on opposite surfaces of the solid electrolyte member 59 are electrode members 63 and 65. The material composition of the solid electrolyte can be satisfied by any of many compositions of materials well known in the art which support oxygen ion conductivity. Such material compositions are described in U.S. Pat. No. 3,400,054, issued Sept. 3, 1968 and incorporated herein by reference. A requirement for the electrode members 63 and 65 is that they provide sufficient electronic conductivity and are operable at elevated temperatures.

A heater assembly 67 positioned within the tubular support member 61 provides uniform operating temperature for the solid electrolyte cell assembly. Electrical leads from the heater assembly 67 extend within tubular member 25, through interconnect member 29 to temperature controller 33.

A suitable composition for the solid electrolyte 59 includes a composition of zirconia and oxides of calcium or related material which provide sufficient oxygen ion conductivity to render the solid electrolyte useful for gas measurement. As described in the referenced U.S. patents, the operation of the conventional solid electrolyte sensor cell is such that the electrolyte member 59 responds to a difference in pressure between that of the reference present at electrode 63 and that of the environment of interest present at the electrode 65 by generating an EMF signal which is monitored by the remote measuring apparatus 35 and interpreted as a measurement of the constituent of interest content in the unknown environment present at electrode 65. According to the present application, the environment present at the electrode 65 is a steam environment which is conducted through the porous protective shield member of the protective shield assembly 23 by diffusion and is introduced into a cavity defined by an end portion of a heat conductive cap 69 and the surface of the solid electrolyte member 59 upon which electrode 63 is disposed through apertures 71 in the heat conductive cavity 69. The construction and operation of the solid electrolyte member in conjunction with the electrodes disposed thereon in response to the partial pressure of constituents of interest in the environments being monitored is clearly described in the referenced patents indicated above.

Experimental verification of the process described herein was affected through the use of the Westinghouse Model 132 oxygen probe with flame arrestor which is manufactured by the Combustion Control Division of Westinghouse Electric Corporation located in Orrville, Ohio. The principal use of this Westinghouse oxygen probe is for the in-situ monitoring of excess oxygen for fossil fuel fired utility and industrial boilers and for providing a voltage signal useful in automatic fuel/air feed control systems for optimizing combustion efficiency. The oxygen probe sensor consists of a high temperature solid electrolyte of zirconia calcia equipped with porous platinum electrodes. The output voltage of this probe is found to be consistent with the thermodynamic predictions of the Nernst equation when using air as a reference gas:

$$\text{emf} = \frac{RT}{4F} \ln \frac{P_{O_2}^{ref}}{P_{O_2}} \qquad (1)$$

For a particular gauge, the following equation applies, $$\text{emf} = \frac{RT}{4F} \ln \frac{P_{O_2}^{ref}}{P_{O_2}} + C \qquad (2)$$

where R is the gas constant, T the absolute temperature of the sensing cell, F the Faraday constant, $P_{O_2}^{ref}$ the partial pressure of oxygen in the reference gas, and $P_{O_2}$ the oxygen partial pressure to be measured. C is a cell constant which corrects the deviation from the Nernst equation. Inserting the standard constants and using air (20.95%$O_2$) as the reference gas, equation (1) gives:

$$\text{emf}(mV) = -3.3669 \times 10^{-2} T - 0.0496 \, T \log P_{O_2} \qquad (3)$$

In measuring hydrogen in steam, the relationship between the partial pressures of $O_2$, $H_2$, and $H_2O$ must satisfy the equilibrium constant, $K_p$, of reaction of formation of water vapor at the cell temperature, $$K_P = P_{H_2O}/(P_{H_2} \cdot P_{O_2}^{\frac{1}{2}})$$

So that equation (3) becomes $$\text{emf (mV)} = -3.3669 \times 10^{-2} T + 0.0992 \, T \log \qquad (4)$$

$$\left( \frac{P_{H_2}}{P_{H_2O}} \cdot K_P \right)$$

Figure 3:
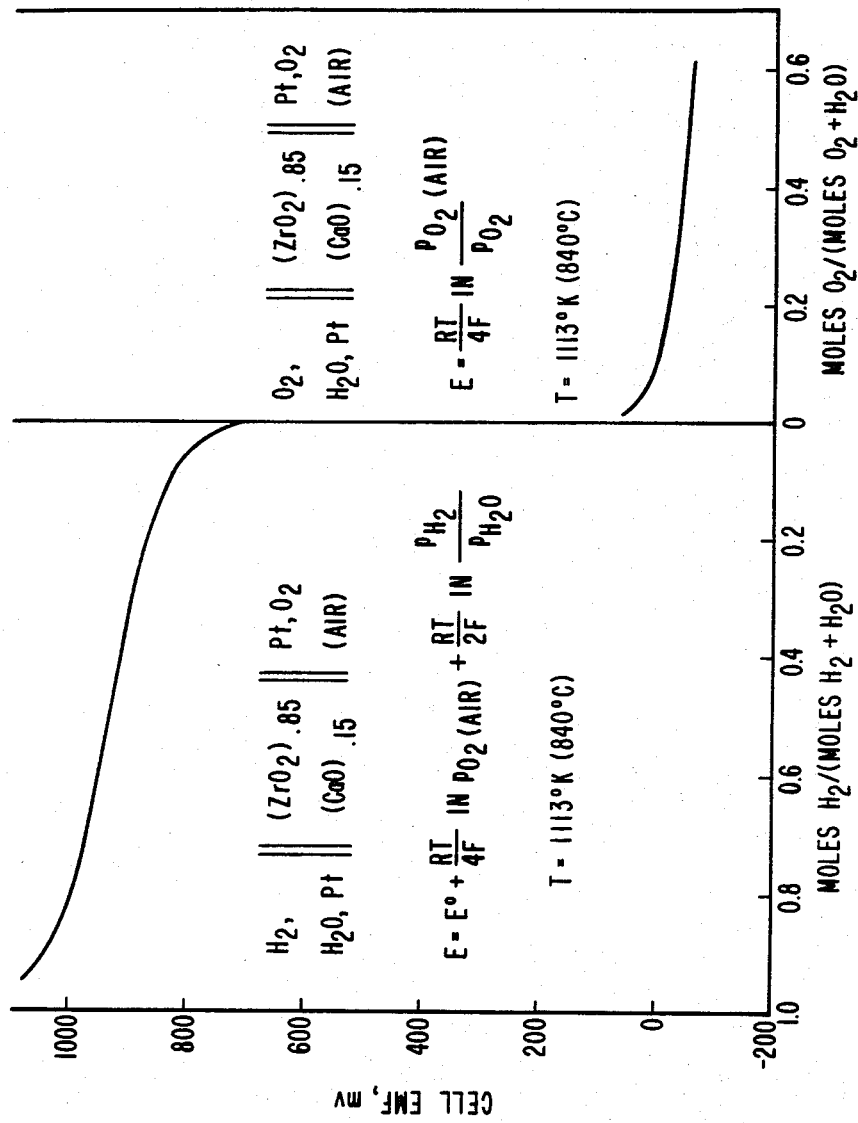
FIG. 3 is a graph demonstrating the theoretical emf versus mole fraction of $H_2$ in $H_2O$—$H_2$ and of $O_2$ in $H_2O$—$O_2$ system at 840° C.

A sharp variation of probe output voltage, ranging from 200 to 900 millivolts, occurs at a transition from fuel rich gas mixture to lean gas mixture, or vice versa. Similar relations can be obtained from steam-$H_2$ equivalent to fuel rich and steam-$O_2$ systems by a calculation based on equations (3) and (4) above. A typical example is illustrated in FIG. 3 in which the schematic cell structures and the Nernst equations are included. The zero at the center of the coordinate represents pure steam.

In power plant steam systems, the range of oxygen or hydrogen partial pressures of interest is within $10^{-9}$ to $10^{-6}$ atm. which is equivalent to a concentration approximately within 1 to 1,000 ppb. The upper limit is lower by three orders of magnitude than that in combustion systems. In order to make possible the use of the probe for the purpose of monitoring such low levels of oxygen and hydrogen in a steam environment without sacrificing the performance stability, it has been found to be advantageous to modify the probe operating temperature. The probe's operating temperature is reduced to 500° C., the selection of which temperature is based on an interrelation between the pressure and temperature dependence of the probe voltage and the thermal disassociation partial pressures of steam in the vicinity of the probe anode, that is, the outer electrode exposed to steam. The probe will not be sensitive for measuring oxygen or hydrogen partial pressures in steam when these values are lower than the steam disassociation partial pressure at the probe temperature.

In order to test the process of this invention, a Westinghouse Model 132 oxygen probe was installed in the main steam supply adjacent to a boiler of a building heating system with saturated steam, at temperature of 114° to 116° C. under a pressure of 1.7 atmosphere under normal mode of operation. The probe used incorporates means for in-situ calibration using standard gas mixtures. Standard hydrogen nitrogen and oxygen-nitrogen mixtures from high pressure cylinders were used for calibration purposes periodically throughout the testing period.

Figure 4:
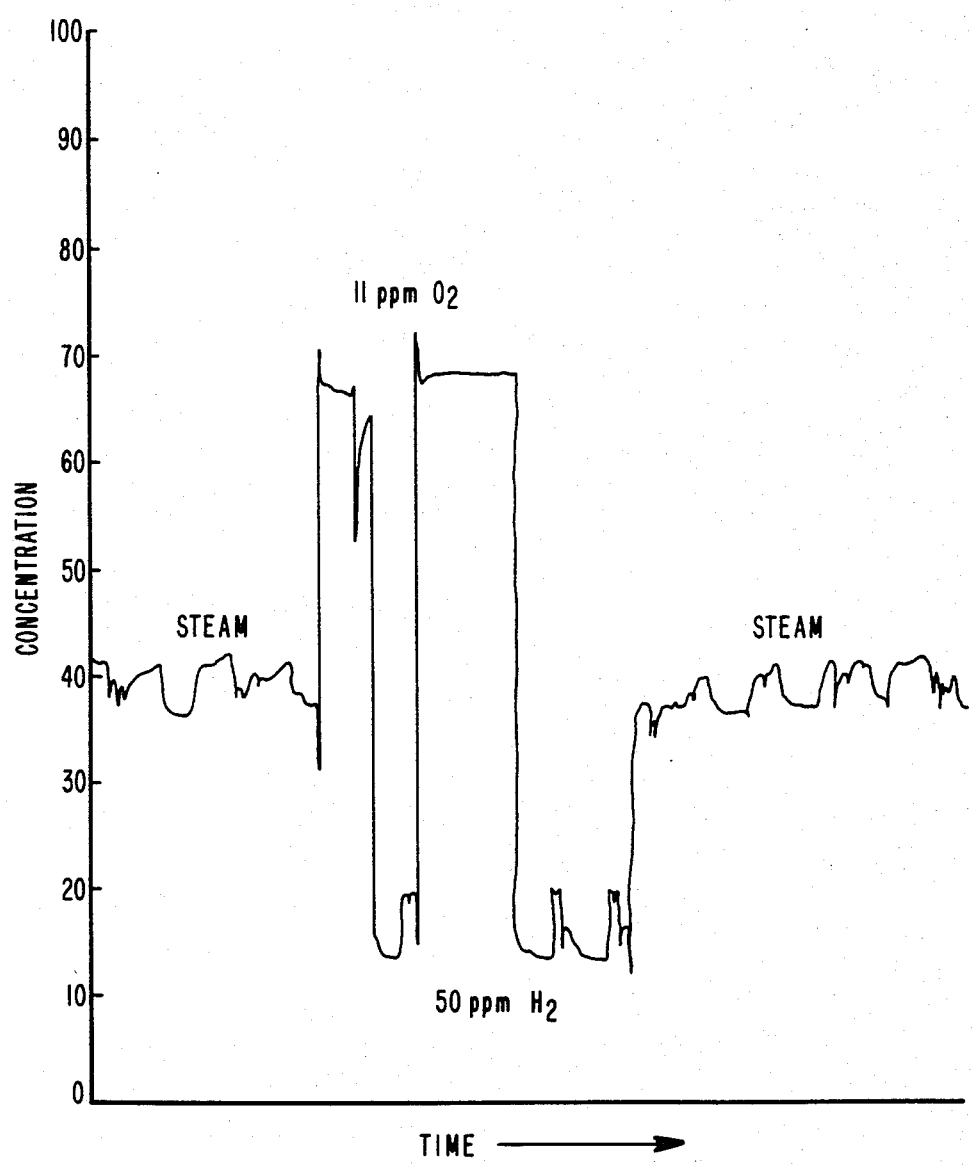
FIG. 4 is a recorder trace of hydrogen (50 ppm) and oxygen (11 ppm) in-steam calibration for a Westinghouse Model 132 Oxygen Probe.

Gas mixtures containing 50 ppm. hydrogen and nitrogen and 11 ppm oxygen and nitrogen were used for the in-situ calibrations of the sensor. Ideally, it is preferable to use calibration gases contained in a steam matrix. However, at the 500° C. probe temperature, both steam and nitrogen are relatively inert and the calibration gases used should agree with those contained in a steam matrix. The probe voltage output was displayed on a pen recorder and the recorder tracing obtained during steam probe calibration with hydrogen and oxygen mixtures as illustrated in FIG. 4. The trace shows a rapid and reproducible response to each calibration gas and a fast return to the original voltage reading for the steam.

Calibration data obtained over an extended testing period indicate that probe calibrations for hydrogen and oxygen remained relative unchanged over the entire test period. The calibration data provide assurance that the output voltage changes observed for the steam reflect changes in steam composition.

A probe operated according to the teachings of this invention has survived continuous operation in steam at 1.7 atmospheres at a temperature of 500° C. for extended periods while providing optimum performance. It has been determined that lowering the cell temperature to 500° C. while operating in a steam matrix makes possible the detection of as little as 1 ppb of reducing gas or 1 ppb of oxidant. Reducing gases possibly present in the steam include hydrazine, ammonia, hydrogen, and organics. When these are present at high levels of approximately 100 to 1000 ppb, the sensitivity for detecting an oxidant at low levels is impaired and reduced to near the fuel level since the cell provides a measure of the concentration residue after fuel/oxygen reaction on the high temperature platinum electrode. A similar situation holds and impairs the monitoring of low levels of reducing agent levels in the presence of high oxygen levels. However, it is this equilibrium reaction response which makes the oxidation/reduction potential so valuable in forecasting gaseous-solids reactions. In fact, the forecasting of gaseous-solids reaction using the oxygen probe is somewhat analogous to forecasting liquids-solids reaction using a pH meter. It really need not be mentioned that the pH meter is not applicable to forecasting gas-solid reactions in superheated steam and the high temperature oxygen probe is not applicable to the forecasting of liquid-solids reactions in the condensate. However, both systems are very sensitive in a selected region of measurement, the pH meter on small departures from neutrality and the oxygen probe on small departures from a stoichiometric mixture. Because fuel and oxidant levels in the steam seldom exceed one part per million in normal plant operations, the oxygen probe sensor retains at least a sensitivity of the order of one part per million for either fuel or oxidant under all normal operating conditions.

It is expected that the probe response to hydrazine will be similar to that for ammonia and therefore, if other reducing agents levels are low compared to the total of hydrazine and ammonia, the oxygen probe output will monitor the level of these and associated changes. Operating thusly, a decrease in the probe voltage output could be indicative of an air leak wherein the oxygen reaction resulted in sufficient concentration lowering of the hydrazine. A maximum voltage output could be indicative of no air inleakage. Knowledge of the oxidation/reduction potential characteristics of the steam and its changes and plant operation would be valuable fault diagnostic information. That information is not available at present in any operating plants and is a situation which is remedied by the technique of this invention. Few, if any, chemical excursions of significance could occur in the secondary cycle and not influence either the pH reading of the condensate or the oxidation/reduction potential characteristic of the gaseous phase or both.

The subatmospheric regions of the power plant are the most vulnerable for air leakage. These include, for example, a part of the low pressure turbine, the condenser, pumping lines to the condenser and the condenser pumps. In most plants, a rotameter is the only monitor for air inleakage into the subatmospheric parts of the secondary cycle and, in general, it is only operative a fraction of the time and provides no remote readout signal.

Figure 5:
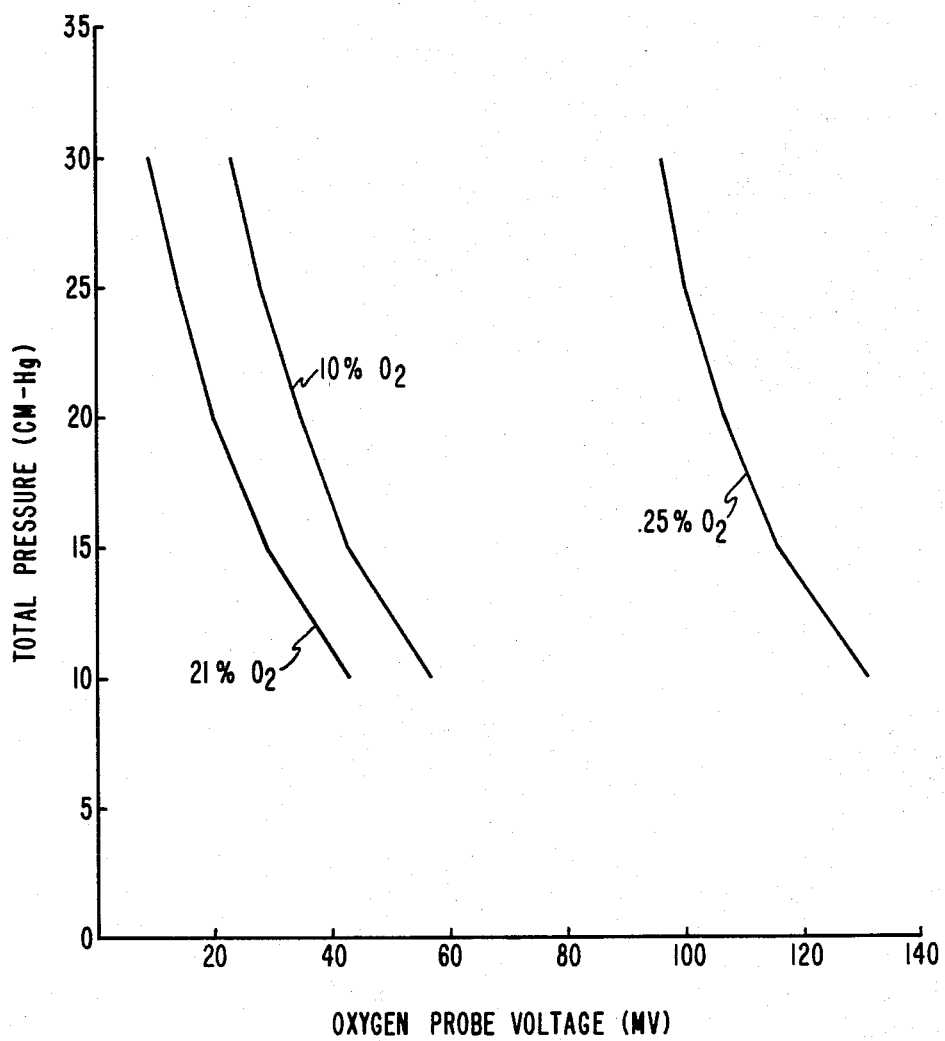
FIG. 5 is a graph demonstrating the total gas pressure versus cell voltage for three gas mixtures of oxygen and nitrogen.

The previously-described oxygen probe has also been tested at subatmospheric pressure for three oxygen containing gas mixtures. The results of this test are presented in FIG. 5 in which the total gas pressure versus probe voltage is presented for three oxygen containing gas mixtures over an absolute pressure range of between 5 to 30 cm. of mercury. The probe response demonstrates the potential usefulness of this invention in measuring subatmospheric oxygen pressures within a range found in condenser pumping lines. Alternatively, this type sensor can also have utility in monitoring oxygen flow rate in the pumping line and for leak detection. In demonstrating the capability of the in-situ probe sensor for continuously monitoring the oxidation/reduction potential characteristic of steam, it has been found advantageous to lower the probe operation temperature from 840° C. to 500° C. This is a requirement for attaining the probe sensitivity capable of detecting oxygen/hydrogen in the low parts per billion range in a steam matrix.

Figure 6:
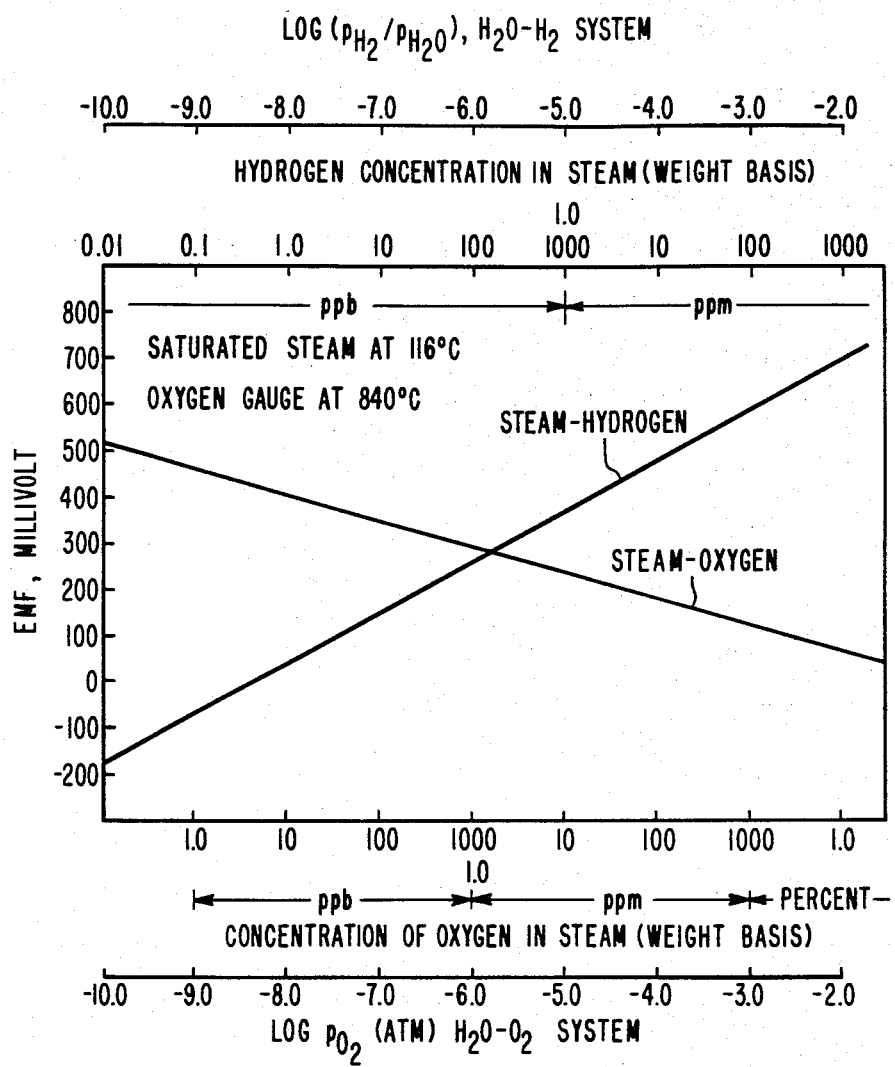
FIG. 6 illustrates the linear relationship between the cell voltage and partial pressure of oxygen and hydrogen in a steam system at 840° C.

The Nernst equation (equation 1) indicates a linear temperature dependence of the emf. The solid oxide electrolyte currently used is a calcia-stabilized zirconia ($\sim$15 mole % oxygen vacancies) and its usual operating temperature is in the range of 600° to 800° C. The linear relationship between the probe voltage and the measured partial pressures or pressure ratios shown in equations 3 and 4 is illustrated in FIG. 6. In FIG. 6, at probe operation temperature of 840° C., the two straight lines representing steam-$H_2$ and steam-$O_2$ systems, separately, cross each other. Beyond the crossing point, each probe voltage output can find two values, one on each line. At the curve intersection, the emf from equation 3 equals that from equation 4 and the numerical value of $P_{O2}$ equals that of $P_{H2}/P_{H2O}$. Then $$\log P_{O2} = \log (P_{H2}/P_{H2O}) = -\frac{2}{3} \log K_P \qquad (5)$$

This relationship applies to the oxygen gauge without regard to the reference gas. However, for the calculation of the emf at the intersections, the reference gas must be specified.

The calculated log ($P_{O2}/P_{H2O}$) and the corresponding emf (using air as the reference gas) at the curve intersections of temperatures 800, 700, 600, and 500° C. are tabulated in Table I; also included in the table are the estimated concentrations of oxygen and hydrogen in saturated steam (116° C.). When the gauge operating temperature is lowered from the present 840° C. to 600° C. or 500° C., the only problem point, when $O_2$ and $H_2$ cannnot be distinguished, is at the output emf of 315 mV (14 ppb $O_2$ or 1.6 ppb $H_2$) or 328 mV (0.75 ppb $O_2$ or 0.09 ppb $H_2$), respectively. Beyond this reading, higher output measures the concentration of hydrogen and lower output measures the concentration of oxygen in steam. Concentrations on the left side of the intersection become insignificant and well below the present detection limit.

TABLE I

Equivalent Pressure Point of Measurements in Steam-Oxygen and Steam-Hydrogen Systems

| Operating Temperature °C. | $\log P_{O_2} = \log \left( \dfrac{P_{H_2}}{P_{H_2O}} \right)$ | emf, mV* | Estimated Concentration, ppb $O_2$ | $H_2$ |
|---|---|---|---|---|
| 800 | −6.12 | 289.6 | 880 | 100 |
| 700 | −6.95 | 302.5 | 150 | 17 |
| 600 | −7.96 | 315.3 | 14 | 1.6 |
| 500 | −9.23 | 328 | 0.75 | 0.09 |

*At equivalent pressure point

The sensitivity of the oxygen probe to oxygen and hydrogen in steam also depends on the partial pressures of the thermally dissociated steam at equilibrium in the vicinity of the probe anode at the anode temperature. The equilibrium composition of thermally dissociated steam at the temperatures of interest has been calculated and is summarized in Table II. In Table II, the partial pressures of hydrogen and oxygen in equilibrium with steam decrease in steps from $10^{-6}$ to $10^{-9}$ atm and from $10^{-7}$ to $10^{-10}$ atm, respectively, as the temperature decreased from 800° to 500° C., successively. In order to measure oxygen and hydrogen in steam in the low (1 to 10) ppb range, the appropriate probe temperature is below 600° C. or at 500° C. This confirms that the reduction of the probe working temperature is required for the present application.

TABLE II

Equilibrium Composition of Pure Steam at Several Temperatures
Total pressure 1.724 atm. (saturated steam at 116° C.)

| Partial Pressure $P_i$, atm | Oxygen gauge operating temperatures, °C. | | | |
|---|---|---|---|---|
| | 800 | 700 | 600 | 500 |
| $P_{H_2O}$ | 1.72399 | 1.72399 | 1.72399 | 1.72399 |
| $P_{H_2}$ | $1.3868 \times 10^{-6}$ | $2.06 \times 10^{-7}$ | $1.99 \times 10^{-8}$ | $1.06 \times 10^{-9}$ |
| $P_{O_2}$ | $6.7 \times 10^{-7}$ | $1.01 \times 10^{-7}$ | $9.86 \times 10^{-9}$ | $5.27 \times 10^{-10}$ |
| $P_{OH}$ | $7.52 \times 10^{-8}$ | $7.26 \times 10^{-9}$ | $4.0 \times 10^{-10}$ | $1.1 \times 10^{-11}$ |
| Concentration μg/kg | | | | |
| $H_2$ | 90 | 13.4 | 1.29 | 0.07 |
| $O_2$ | 695 | 104 | 10.2 | 0.55 |
| OH | 41 | 3.9 | 0.21 | 0.006 |

The oxygen and hydrogen contents in steam directly reflect the degree of oxidizing and reducing conditions of the steam, respectively. The extent of variation of each condition and the frequency of transition from one condition to the other, may affect the stability of construction metal and metal oxides in the metal system. Metals can be oxidized by oxygen or steam but the metal oxides (the scales) may also be reduced in the presence of hydrogen. Interaction between the deposited oxide and the metal substrate may occur at certain conditions. The oxygen gauge responded to hydrogen and also hydrogen-containing, combustible additives such as hydrazine in steam. Since hydrazine is also a reducing agent, interaction of hydrazine vapor and solid metal oxides can, therefore, be controlled by the hydrogen levels in steam.

Figure 7:
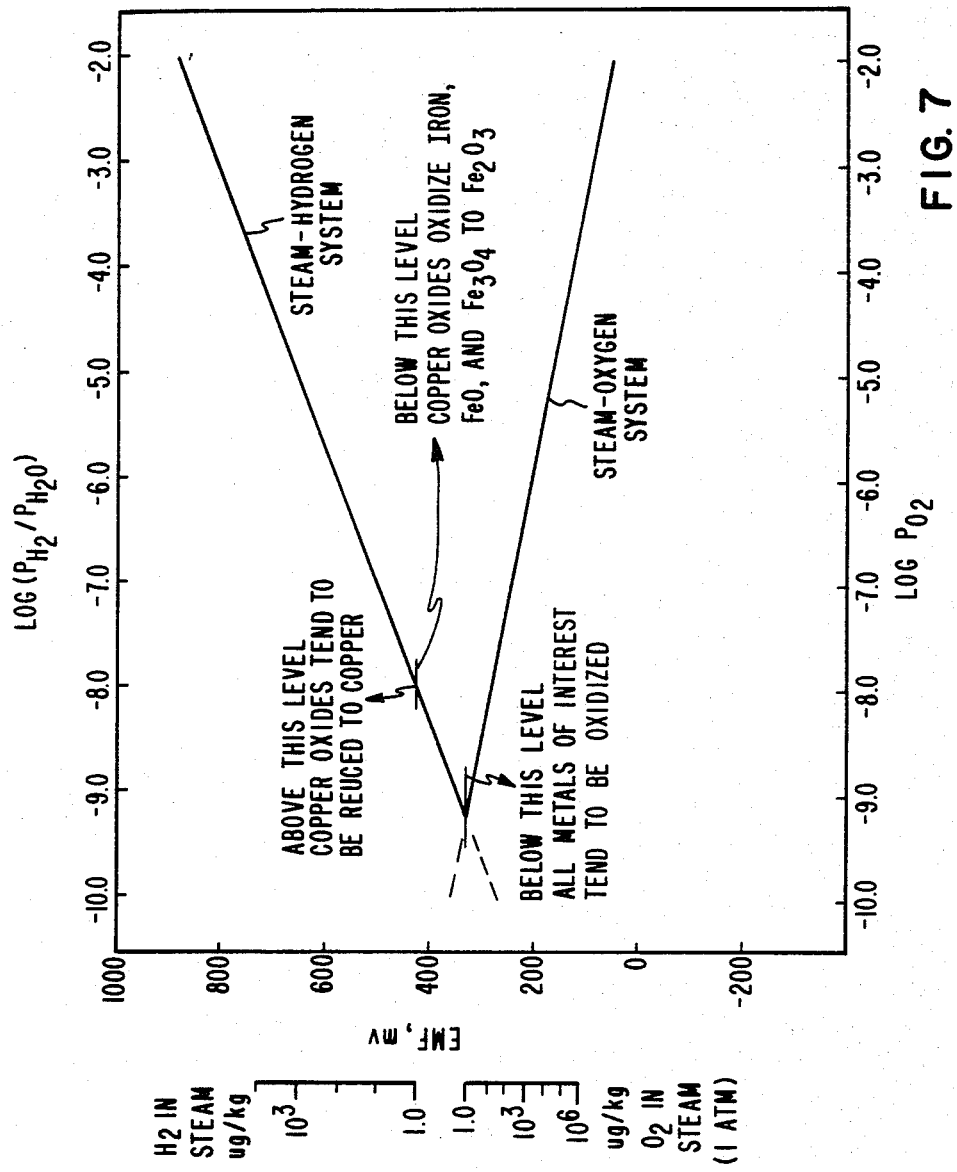
FIG. 7 represents the calculated output voltage of the sensor assembly at an operating temperature of 500° C. plotted against $P_{O_2}$ and $P_{H_2}/P_{H_2O}$ and the stable regions for metal and metal oxides.

A calculated output voltage of the oxygen gauge at working temperatures of 500° C. is plotted against $P_{O_2}$ and $P_{H_2}/P_{H_2O}$ in FIG. 7. At this probe working temperature, as discussed above, the probe is expected to be sensitive to oxygen and hydrogen in the low ppb range as predicted. In FIG. 7, the scales of hydrogen and oxygen are superimposed. A bar is added to the hydrogen curve at log $(P_{H_2}/P_{H_2O})$ of −8.0 which is equivalent to a hydrogen concentration in steam at 1 ppb and a theoretical voltage of 422.6 mV. Thermodynamically, above this level, copper oxides tend to be reduced to copper in the steam. Below this level, copper oxides have a tendency to oxidize iron, nickel, and cobalt into the corresponding oxide or oxides (e.g. $Fe_3O_4$ and $Fe_2O_3$) and strongly influence the metal, especially the iron transport. Also, a bar is added to the oxygen curve nearby but below the crossing point of the curves, at oxygen concentration of 1 ppb. Probe output below this bar indicates a higher oxygen content and all the construction metals of interest tend to be oxidized.

What has been described is a method for operating a solid electrolyte electrochemical cell assembly and a method for monitoring the oxidation/reduction potential characteristics of a steam environment of interest. While particular attention has been given to the use of in-situ probe assemblies, it is, of course, possible to use an ex situ probe to affect the technique of this invention.

Having thus described the invention, what is claimed is:

1. A method of operating a solid electrolyte electrochemical cell assembly in a steam environment for the purpose of monitoring the oxidation/reduction potential of the environment, said solid electrolyte electrochemical cell assembly being of the type in which the solid electrolyte electrochemical cell is a solid electrolyte member having a first electrode disposed in contact with a first surface of the solid electrolyte member and a second electrode disposed in contract with the opposite surface of the solid electrolyte member, the solid electrolyte member is disposed in the cell assembly such that the first surface of the solid electrolyte member is exposed to a reference gas and the opposite surface of the solid electrolyte member is exposed to an environment of interest such that an electrical signal reflecting the gas partial press is generated, and the cell assembly includes heating means operatively associated therewith for effecting the controllable heating of the solid electrolyte member, said operational method comprising the steps of:

disposing the cell assembly in a steam environment such that the second surface of the solid electrolyte member is in communication with the steam environment, providing a reference gas of determinable content in communication with the first surface of the solid electrolyte member, heating the solid electrolyte member by means of said heating means operatively associated therewith to a temperature of about 500° C. at which low concentration levels of oxygen and hydrogen are distinguished from one another, and measuring the electrical signal generated by the solid electrolyte member as a function of the oxygen or hydrogen content in the steam environment.

2. The method of operating a solid electrolyte electrochemical cell according to claim 1 wherein the reference gas in communication with the first surface of the solid electrolyte member is air with a known oxygen content.

3. The method of operating a solid electrolyte electrochemical cell according to claim 1 wherein the reference gas is an oxygen containing inert gas.

4. The method of operating a solid electrolyte electrochemical cell according to claim 1 wherein the solid electrolyte member is a solid electrolyte selected from the group consisting of $ZrO_2$—$CaO$, $ZrO_2$—$Y_2O_3$ and $ThO_2$—$Y_2O_3$.

5. A method for monitoring the concentration of oxygen or hydrogen in a steam environment with a solid electrolyte electrochemical cell comprising the steps of:

sampling the steam environment with the solid electrolyte electrochemical cell assembly of about 500° C.;

determining the partial pressure of the sample contacting the solid electrolyte electrochemical cells assembly;

establishing a set of predetermined criteria, said criteria reflecting the oxygen or hydrogen content in a steam environment; and comparing said determined partial pressure of said sample with said set of predetermined criteria.

* * * * *